United States Patent
Rosoff et al.

(10) Patent No.: US 7,011,650 B2
(45) Date of Patent: Mar. 14, 2006

(54) MULTIPLE-DOSE SYRINGE WITH COLLAPSIBLE CONTAINER

(75) Inventors: Jack P. Rosoff, Portland, OR (US); Michael N. Hirsch, Portland, OR (US); Ali S. Salem, Canby, OR (US)

(73) Assignee: Paradigm Medical, LLC, Portland, OR (US)

( * ) Notice: Subject to any disclaimer, the term of this patent is extended or adjusted under 35 U.S.C. 154(b) by 0 days.

(21) Appl. No.: 10/336,977

(22) Filed: Jan. 6, 2003

(65) Prior Publication Data

US 2003/0167041 A1 Sep. 4, 2003

Related U.S. Application Data

(63) Continuation-in-part of application No. 09/923,756, filed on Aug. 6, 2001, now Pat. No. 6,558,358, which is a continuation of application No. 09/392,870, filed on Sep. 9, 1999, now Pat. No. 6,270,482, application No. 10/336,977, and a continuation-in-part of application No. 10/093,707, filed on Mar. 7, 2002, now abandoned.

(60) Provisional application No. 60/274,669, filed on Mar. 8, 2001.

(51) Int. Cl.
*A61M 5/178* (2006.01)
(52) U.S. Cl. .................. 604/216; 604/191; 604/212
(58) Field of Classification Search .............. 604/68, 604/70, 71, 181, 187, 212, 214, 216, 191
See application file for complete search history.

(56) References Cited

U.S. PATENT DOCUMENTS 2,939,459 A 6/1960 Lazarte et al. .............. 128/218
2,950,717 A 8/1960 Bouet .......................... 128/218
3,911,916 A 10/1975 Stevens ....................... 128/218
4,175,704 A * 11/1979 Cohen ......................... 604/198

(Continued)

FOREIGN PATENT DOCUMENTS

DE 3618318 C2 12/1987

(Continued)

*Primary Examiner*—LoAn H. Thanh
(74) *Attorney, Agent, or Firm*—Paul J. Fordenbacher, Esq.; Silicon Forest Patent Group

(57) ABSTRACT

A multiple-dose syringe including a barrel with a closed end and an open end, the closed end having an injection port that may be adapted to receive a needle, or that may be adapted to engage a commercially available needle-less system for fluidly connecting a syringe to an IV or a medicine vial. A plunger is slidably disposed through the open end of the barrel. A container is connected to an end of the plunger to move with the plunger. The container has a deformable shell with an opening at a forward end thereof and a predetermined quantity of fluid sealed therein by a closure member disposed over the opening to selectively seal the opening. The closure member includes a valve that opens in response to a fluid pressure differential across the valve. The container is slidably disposed in the barrel and includes a seal proximal to the forward end to form a first cavity in the barrel with a volume that is adjustable by moving the container in the barrel with the plunger so that fluid can be selectively drawn into and expelled from the first cavity, which is contiguous to the injection port. After at least a substantial portion of the fluid is expelled from the first cavity, the shell is configured to be collapsed by further pressure applied by the plunger, and after a predetermined fluid pressure differential across the closure member is reached, the valve of the closure member opens to allow expulsion of the quantity of fluid contained in the container.

3 Claims, 15 Drawing Sheets

U.S. PATENT DOCUMENTS

| | | | |
|---|---|---|---|
| 4,215,701 A | 8/1980 | Raitto | 128/763 |
| 4,439,184 A | 3/1984 | Wheeler | 604/90 |
| 4,702,737 A | 10/1987 | Pizzino | 604/191 |
| 4,715,854 A | 12/1987 | Vaillancourt | 604/191 |
| 5,281,198 A | 1/1994 | Haber et al. | 604/86 |
| 5,308,322 A | 5/1994 | Tennican et al. | 604/83 |
| 5,489,267 A | 2/1996 | Moreno et al. | 604/89 |
| 5,637,087 A * | 6/1997 | O'Neil et al. | 604/82 |
| 5,720,731 A | 2/1998 | Aramata et al. | 604/191 |
| 6,077,252 A | 6/2000 | Siegel | 604/214 |
| 6,270,482 B1 * | 8/2001 | Rosoff et al. | 604/200 |
| 6,485,471 B1 * | 11/2002 | Zivitz et al. | 604/212 |
| 6,558,358 B1 * | 5/2003 | Rosoff et al. | 604/200 |
| 6,705,756 B1 * | 3/2004 | Botrie et al. | 366/181.5 |
| 6,723,074 B1 * | 4/2004 | Halseth | 604/201 |

FOREIGN PATENT DOCUMENTS

| | | | |
|---|---|---|---|
| FR | 2750051 A | 12/1997 | 315/19 |
| JP | 10-57487 A | 8/1998 | 315/718 |

* cited by examiner

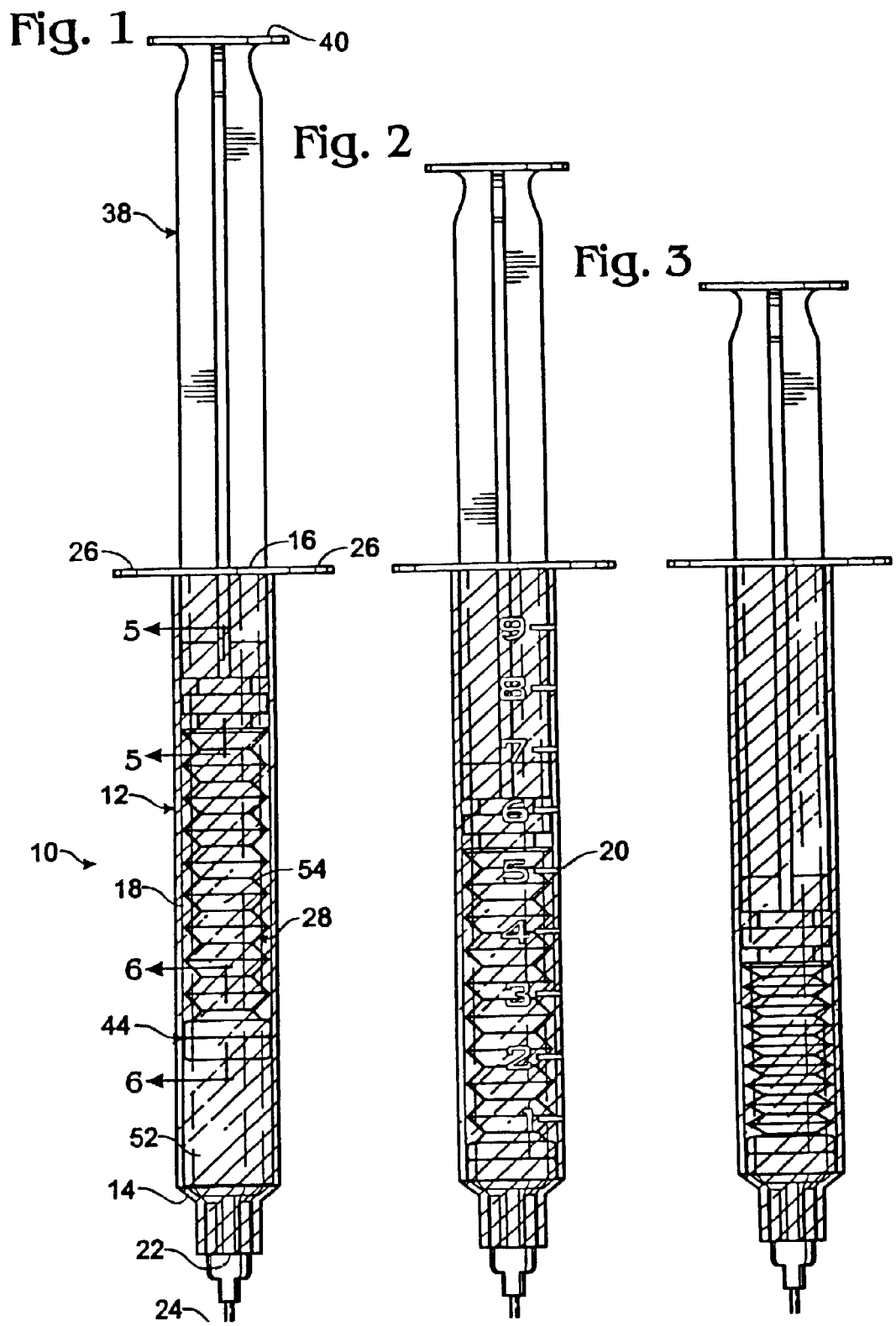

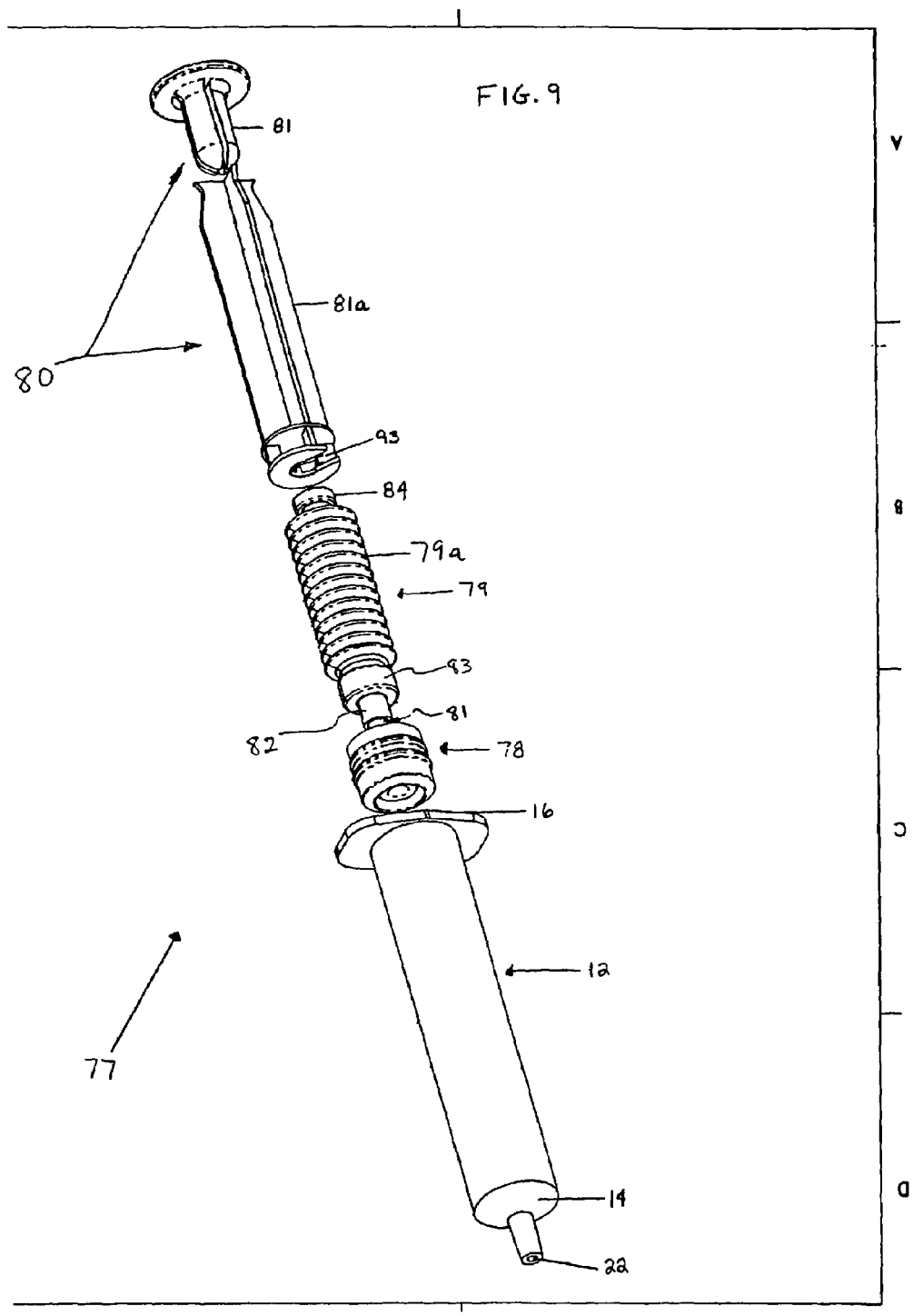

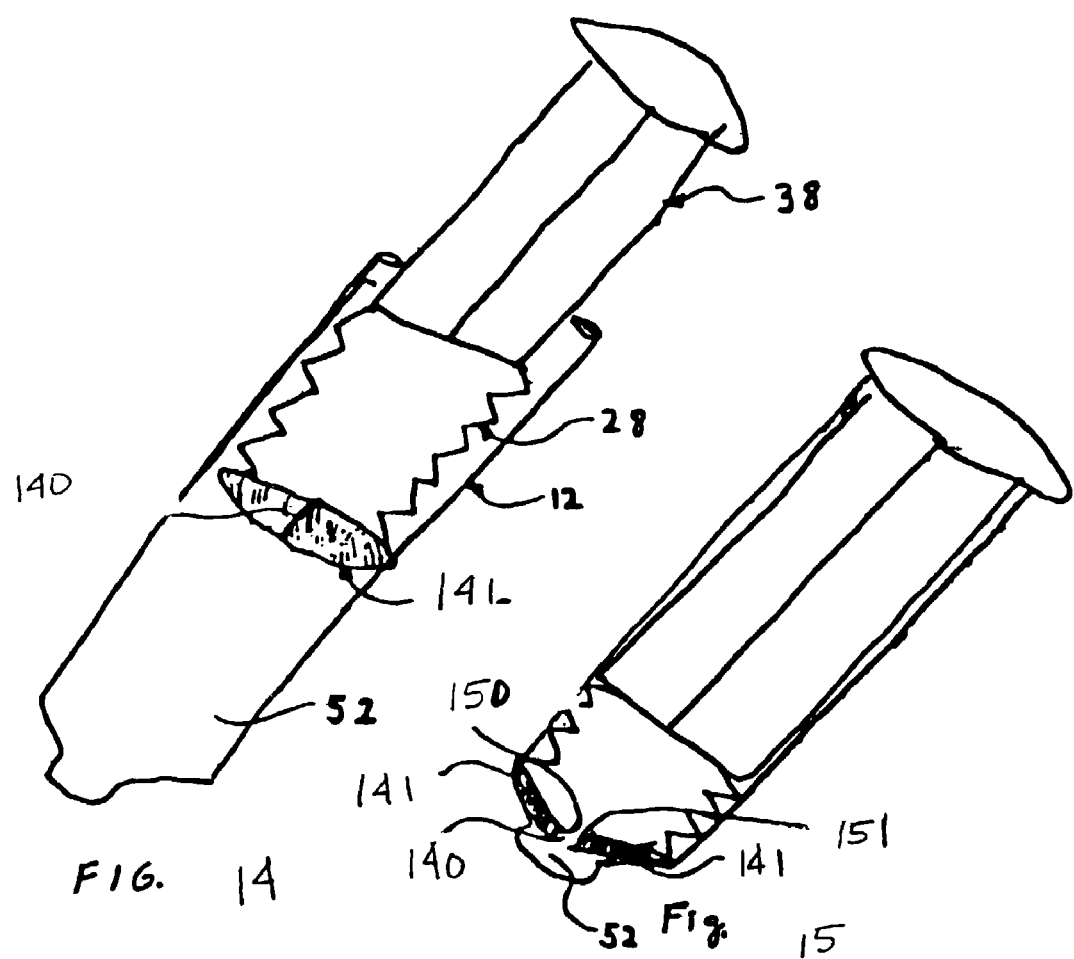

MULTIPLE-DOSE SYRINGE WITH COLLAPSIBLE CONTAINER

REFERENCE TO RELATED PATENT APPLICATIONS

This application claims priority under 35 U.S.C. §120 to and is a continuation in part of U.S. patent application Ser. No. 09/923,756, filed Aug. 6, 2001, now U.S. Pat. No. 6,558,358, entitled "Multiple-Dose Syringe," which is a continuation of U.S. patent application Ser. No. 09/392,870, entitled "Multiple-Dose Syringe," filed Sep. 9, 1999, which issued as U.S. Pat. No. 6,270,482, on Aug. 7, 2001, both of which are incorporated herein by reference in their entirety. This application also claims priority under 35 U.S.C. § 120 to and is a continuation in part of U.S. patent application Ser. No. 10/093,707, filed Mar. 7, 2002, now abandoned, which claims priority under 35 U.S.C. § 119(e)(1) to U.S. Provisional Application Ser. No. 60/274,669 filed Mar. 8, 2001, and which also claims priority under 35 U.S.C. § 120 to U.S. patent application Ser. No. 09/923,756, which is a continuation of U.S. patent application Ser. No. 09/392,870, which is now U.S. Pat. No. 6,270,482. All of the aforementioned patent applications and U.S. Pat. No. 6,270,482 are incorporated herein by reference as if set forth in full.

FIELD OF THE INVENTION

The present invention relates to a syringe, and more particularly, to a syringe adapted to sequentially inject a plurality of fluids.

BACKGROUND OF THE INVENTION

When administering certain medications, it is sometimes necessary to inject sequentially two fluids into a patient. For example, during chemotherapy, small quantities of medicine are administered, usually through an intravenous catheter (i.e., commonly referred to as "IV," and referred to below as an "IV"). To insure that all of the medicine reaches the patient, the medication is followed by a saline flush. The saline flush rinses any residual medicant through the IV and into the patient. Traditionally, the saline flush is administered as a separate step from the medicine. In particular, a standard single-dose syringe is used to deliver the medicine. A health care worker then, preferably, utilizes a second syringe containing the desired quantity of saline. The saline is then injected into the IV to flush the medicine into the patient. This process wastes time because it requires multiple operations, and wastes materials as it requires multiple syringes.

Various types of syringes for dispensing sequentially multiple fluid doses have been proposed to address the above problem. For example, U.S. Pat. No. 4,702,737 to Pizzino discloses a multiple-dose, single-barrel syringe utilizing a plurality of telescoping sections of progressively decreasing diameter. Unfortunately, the design of this syringe requires that all of its chambers be pre-loaded with fluids at the time of manufacture. In particular, the syringe incorporates a needle that extends into the barrel of the syringe to puncture a membrane to release the second fluid. The internal needle prevents the syringe from being completely closed to draw fluid into the barrel. As a result of the need to completely preload the syringe, it is necessary to stock separate syringes for each medication. Such medications are often expensive and have limited shelf life, thereby limiting the usefulness of this design.

U.S. Pat. Nos. 4,439,184, 4,715,854, and 5,720,731 to Wheeler, Viallancourt and Armata, respectively, disclose multiple-dose syringes with two pistons and a bypass zone. In each of these patents, a second chamber between the first and second pistons is filled and dispensed through the bypass zone, which is located on one side of the barrel wall near the injection port. Syringes with a bypass zone and multiple pistons are complicated to manufacture and require many specially designed parts. In most of the floating piston designs, the syringe must be preloaded with both fluids because the syringe cannot draw fluids or aspirate. In addition, the floating piston is subject to jamming and may thereby become difficult to depress.

BRIEF DESCRIPTION OF THE DRAWINGS

FIG. 1 is a side view of a syringe constructed according to the present invention.

FIG. 2 is a side view of the syringe of FIG. 1 with the fluid in a first cavity expelled.

FIG. 3 is a side view of the syringe of FIG. 1 with part of the fluid in a container expelled.

FIG. 9 is an exploded assembly drawing of the best mode embodiment of the multiple-dose syringe of the present invention.

FIG. 14 is a drawing illustrating an alternative embodiment of a multiple-dose syringe with a closure member including a valve that opens in response to a fluid pressure differential.

FIG. 15 is a drawing illustrating the alternative embodiment of a multiple-dose syringe with the valve of the syringe of FIG. 14 in the open state.

DETAILED DESCRIPTION OF THE INVENTIONS

Figure 5:
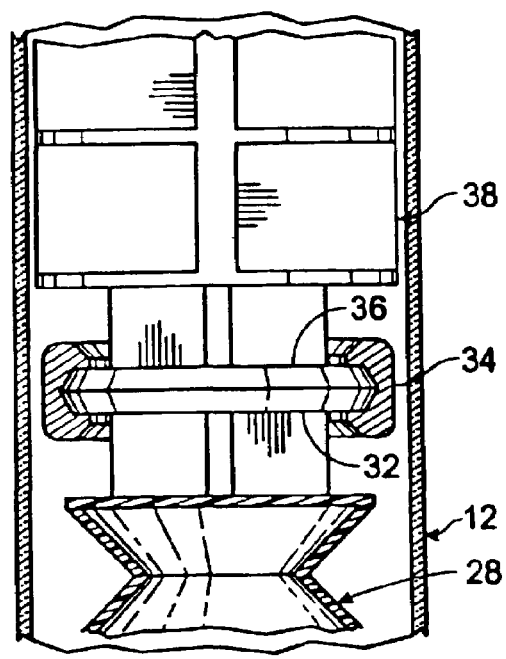
FIG. 5 is an enlarged view of a coupler configured to connect a plunger to the container of FIG. 4.

A syringe constructed according to the present invention is shown generally at 10 in FIG. 1. Syringe 10 includes a cylindrical hollow barrel 12 with a closed end 14 and an open end 16. The cylindrical walls of the barrel define a cavity 18, which is adapted to receive and hold the fluid to be dispensed. The cavity typically has a volume or capacity of between 1 and 10 cc, and is marked with gradations 20 to permit the amount of fluid to be measured. It should, or course, be understood, that the present invention could be implemented with syringes of any size. The closed end has an injection port 22, which may be configured to receive a needle 24. Alternatively and preferably, as shown in FIG. 9b, the closed end 14 has an injection port 22 configured for use with a needle-less coupling system to fluidly connect a syringe to an IV and/or a medicine vial, for example, the coupling system known under the Luer-Lok(™) trademark and manufactured by Becton, Dickinson and Company, Corp., the system used with a "Luer"-type syringe, or any other commercially available needle-less system for fluidly coupling a syringe to a medicine vial and/or an IV. The syringe 12 of FIG. 9b represents a typical needle-less syringe, and has an injection port 22 having an internally threaded sleeve 160 with internal threads 162, and a hollow neck 164 for providing fluid communication between the cavity 18 and an IV. Alternatively, Finger grips 26 are disposed adjacent to the open end of the barrel and allow the user to grasp the barrel when drawing fluids into or dispensing fluids out of the syringe.

Figure 4:
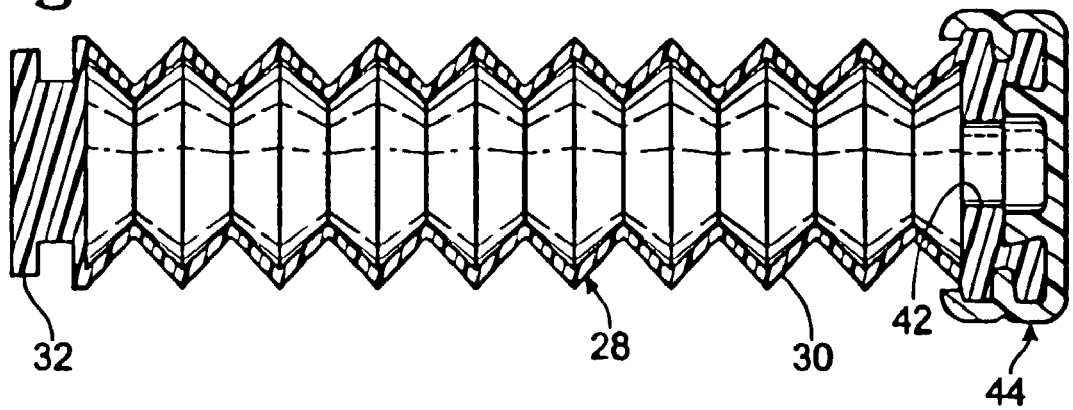
FIG. 4 is a sectional view of a container constructed according to the present invention.

A fluid container 28 is slidably received into barrel 12 through open end 16. As shown in FIG. 4, the container includes a cylindrical bellows-like shell 30. The shell is preferably made of a flexible material that is non-reactive to the fluid stored therein. For instance, polypropylene is a suitable material when the container is used to hold saline. The flexible material allows the container to collapse to dispense fluid, as described in more detail below and illustrated in FIG. 3. It should be understood that other collapsible configurations besides a pleated or bellows structure could be used for shell 30.

As shown in FIG. 5, a connector 32 is formed on a closed end of the shell. Connector 32 is joined by a coupler 34 to corresponding connector 36 formed on the end of a plunger 38. Plunger 38 has an elongate shaft extending from connector 36 to a thumb pad 40, which is shown in FIG. 1 and is used to depress or retract the plunger. Coupler 34 is preferably formed of a butyl rubber compound and deforms to slip over the connectors. The connection between the container and the plunger allows the plunger to be used to move the container up and down in the barrel. As such, many other connections between the container and the plunger could also be used, including, for instance, glue or clips. Also, the plunger could be formed integrally with the container. As is apparent, one of the functions of the plunger is to compress the fluid container within the barrel.

Figure 6:
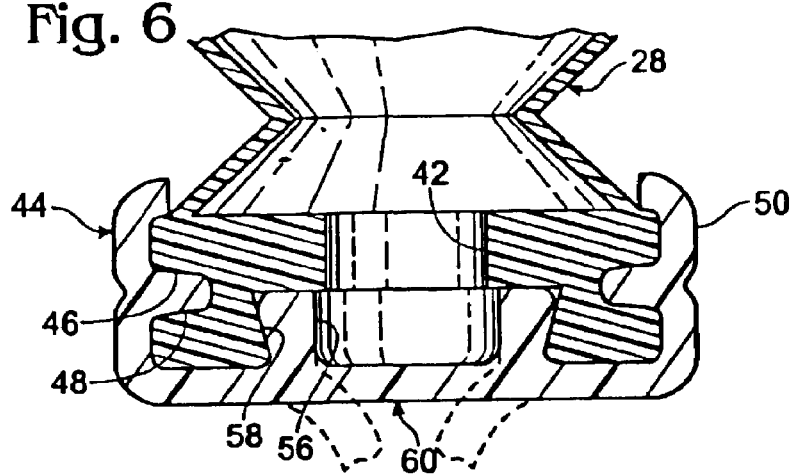
FIG. 6 is a sectional view of a container cap constructed according to the present invention.

The end of the shell opposite connector 32 includes a passage 42 that is selectively sealed by a closure member in the form of a cap 44, as shown in FIG. 6. The shell includes a circumferential groove 46 that receives a corresponding flange 48 formed on the inside surface of the cap. The cap is preferably formed of a butyl rubber compound to allow it to be fitted over the end of the shell and retained thereon. The outer perimeter of the cap is shaped to form a perimeter seal 50 and sized to fit snuggly within the barrel, similar to the tip on a standard plunger. When the container is placed in the barrel, as shown in FIGS. 1–3, the perimeter seal effectively separates the barrel into two regions or cavities: a first region 52 disposed between the closed end and the cap and a second region 54 disposed behind the cap and occupied by the container.

An inwardly facing cup 56 is formed on the end face of the cap as shown in FIG. 4. The walls of the cup are received in a recess 58 formed in the end of the shell proximal to passage 42. A slight outward tilt to the walls of the cup and recess serves to help retain the cap on the end of the shell. In particular, any pressure created in the fluid in the shell tends to urge the walls of the cup outward to tighten the seal between the cap and shell, thereby preventing the escape of fluid and preventing the cap from being pushed off the end of the shell.

The bottom of the cup forms a rupture zone 60 that is pressure rupturable, i.e. ruptures when fluid pressure across the rupture zone exceeds some desired level. For instance, the thickness of the rupture zone may be varied to control the pressure at which rupture occurs. Alternatively, a defect may be created in the rupture zone to provide a predetermined failure location. For example, the defect can be a cut extending part-way through the material of the cap or a series of partial perforations. In general, however, the rupture zone should fail at a relatively predictable pressure. Furthermore, the pressure should be readily achievable by finger pressure on the thumb pad of the plunger. It should be noted that any pressure created in the shell is matched by backpressure of the fluid in the first region. Therefore, zone 60 will not rupture until all the fluid in the first region is substantially expelled. The dashed lines in FIG. 6 depict the rupture zone after rupture.

Figure 7:
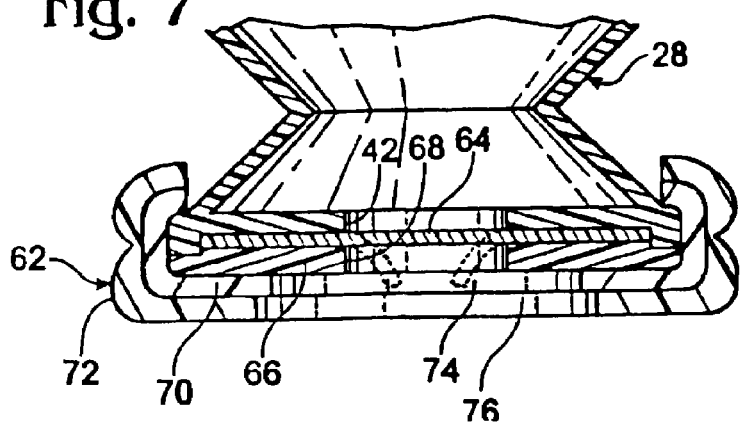
FIG. 7 is an alternative embodiment of the cap of FIG. 6.

An alternative cap structure 62 is shown in FIG. 7 and includes a rupture sheet 64 disposed over passage 42. The rupture sheet is preferably formed of a thin sheet of rubber, plastic or non-corrosive metal. The rupture sheet is supported and retained against the end of the shell by a seal flange 66 with a central aperture 68 aligned with passage 42. The aperture allows fluid to pass after rupture of the sheet. The seal flange is held in place on the end of the shell by a clamp ring 70 that is crimped over the end of the shell. The clamp ring is preferably formed from a thin deformable cylinder of metal, such as used on the end of a medicine vial. A seal 72, preferably formed of a butyl rubber compound, is disposed over the clamp ring to form a seal with the walls of the barrel, as previously described. The clamp ring and seal include apertures 74 and 76, respectively, that allow fluid from the container to pass after the sheet is ruptured, as shown by the dashed lines in FIG. 6.

Figure 8:
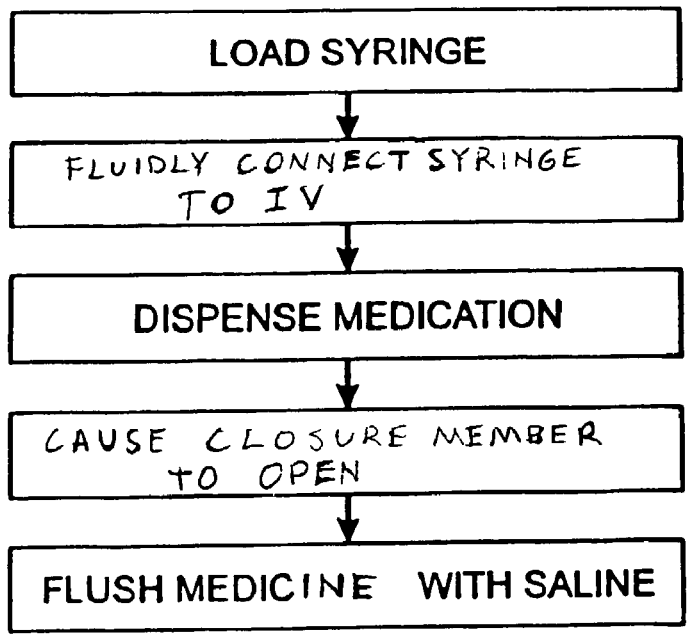
FIG. 8 is a block diagram of the steps involved in utilizing the syringe of FIG. 1.

FIG. 8 depicts the steps involved in using a syringe according to the present invention. First, the operator selects a pre-loaded syringe package and removes the sterile envelope. The fluid container of the pre-loaded syringe package is preferably pre-loaded with a secondary fluid, such as saline. If necessary, a needle may be attached to the barrel. The syringe is then fluidly connected, either by a needle or through a needle-less system (such as shown in FIG. 9b), to a vial containing a primary fluid, such as a medicine. The operator then loads the desired amount of primary fluid, such as a medicine, into the syringe similar to loading a conventional syringe. This is possible because the plunger/container functions like a standard plunger until the medicine in the forward region is expelled. Thus, the operator can retract the plunger to load air into the syringe, connect the syringe to a medicine vial, push forward on the plunger to inject the air into the vial and then retract the plunger again to withdraw the desired amount of medicine. The syringe is then fluidly connected to an IV, either by the insertion of a needle or through a needle-less system (such as shown in FIG. 9b), and the medicine is dispensed by depressing the plunger, as shown by comparison of FIGS. 1 and 2. When the medicine (or other primary fluid) is dispensed, subsequent pressure on the plunger causes a greater fluid pressure differential across the closure member thereby causing the closure member to open, for example, by rupturing (as illustrated in FIGS. 6 and 7), or, preferably, by the opening of a valve (for example, the best mode valve of FIGS. 9, 9a, 9b, 11, and 12, or the valve of FIGS. 14, 15, 16, and 17, or the valve of FIG. 18), thereby releasing the saline or other fluid in the container. The plunger is then further depressed to compress the container, as depicted, for example, in FIG. 3, thereby forcing the saline or other secondary fluid in the container out of the container to flush the medicine (or other primary fluid) through the IV with the saline or other secondary fluid.

Figure 9A:
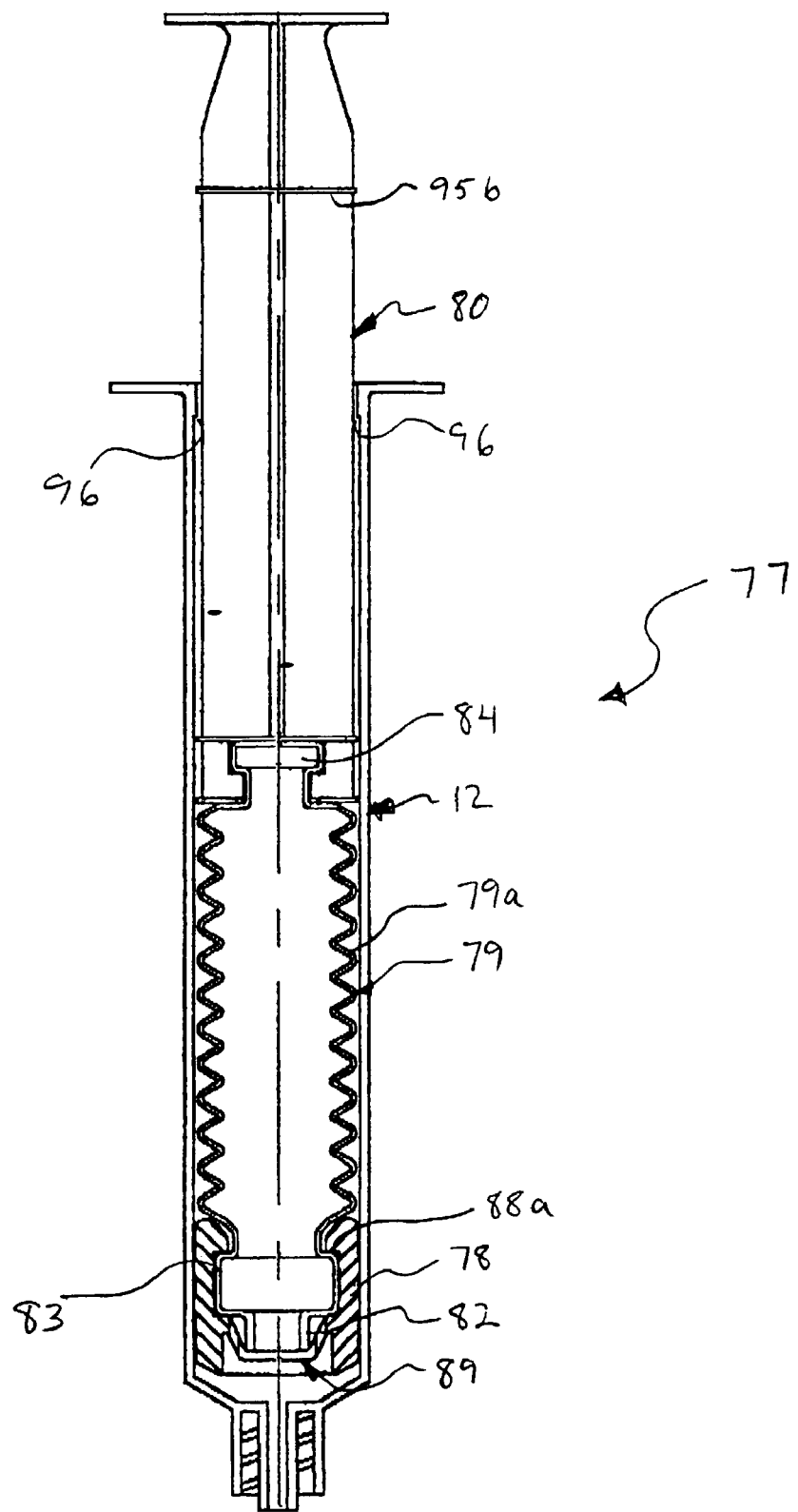
FIG. 9a is an assembly drawing of the best mode embodiment of the multiple-dose syringe of the present invention.
Figure 9B:
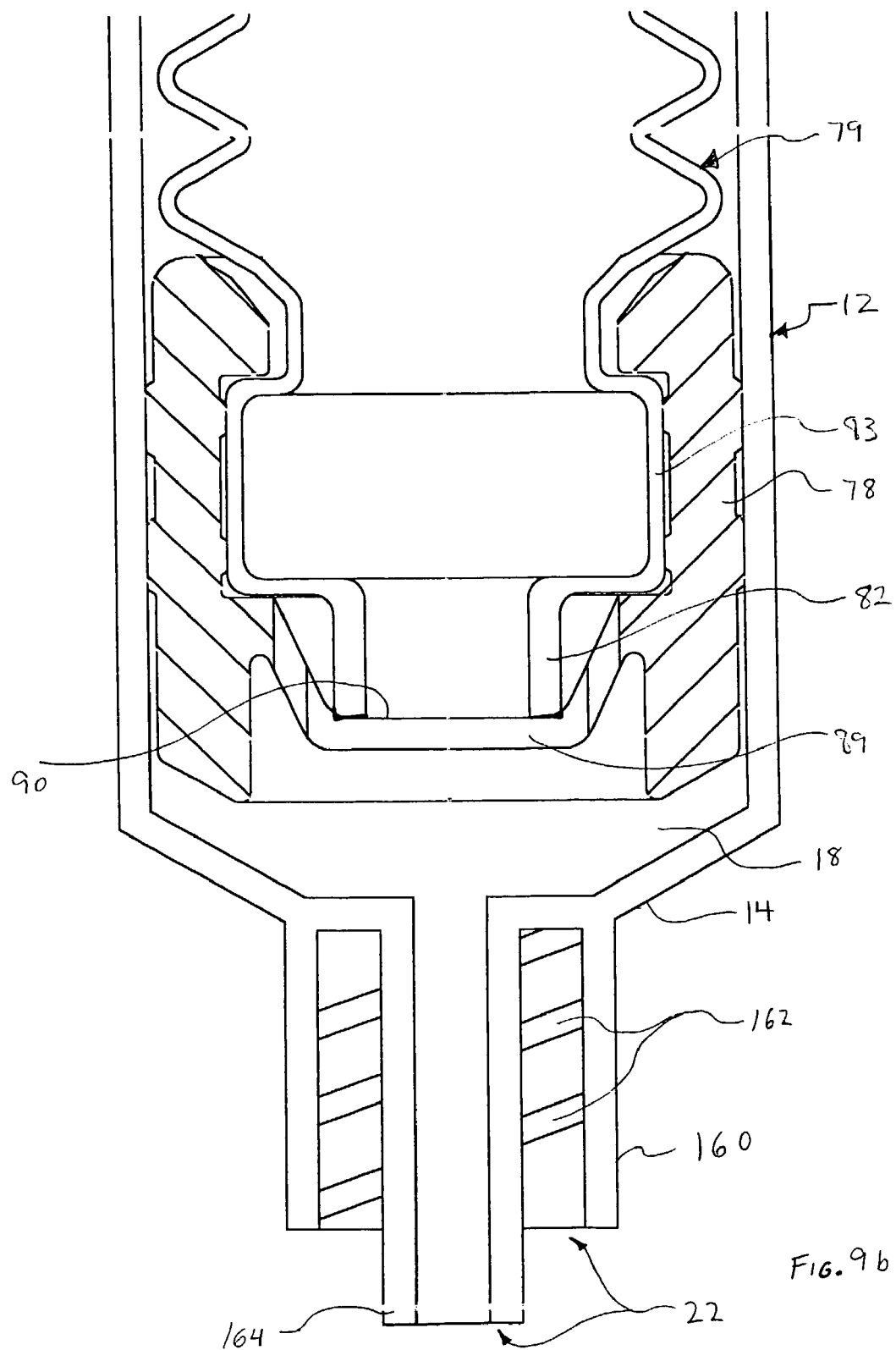
FIG. 9b is a close-up view of one end of the assembly drawing of FIG. 9a showing the assembly of the closure member and the container in more detail.

Alternatively, the best mode of practicing the inventions claimed herein is shown in FIGS. 9 and 9a, which illustrate an alternative embodiment of a multiple-dose syringe 77 with a closure member 78 including a valve that opens in response to a fluid pressure differential. Syringe 77 includes the cylindrical hollow barrel 12 discussed above, including a closed end 14 and an open end 16. As discussed above, the closed end 14 has an injection port 22 which is configured to receive a needle.

The syringe 77 further includes a closure member 78, a fluid container 79, plunger 80, which includes a thumb pad 81 and elongate shaft 81a. As shown in FIG. 9, the closure member 78 is slidably received into barrel 12 through open end 16.

Figure 10:
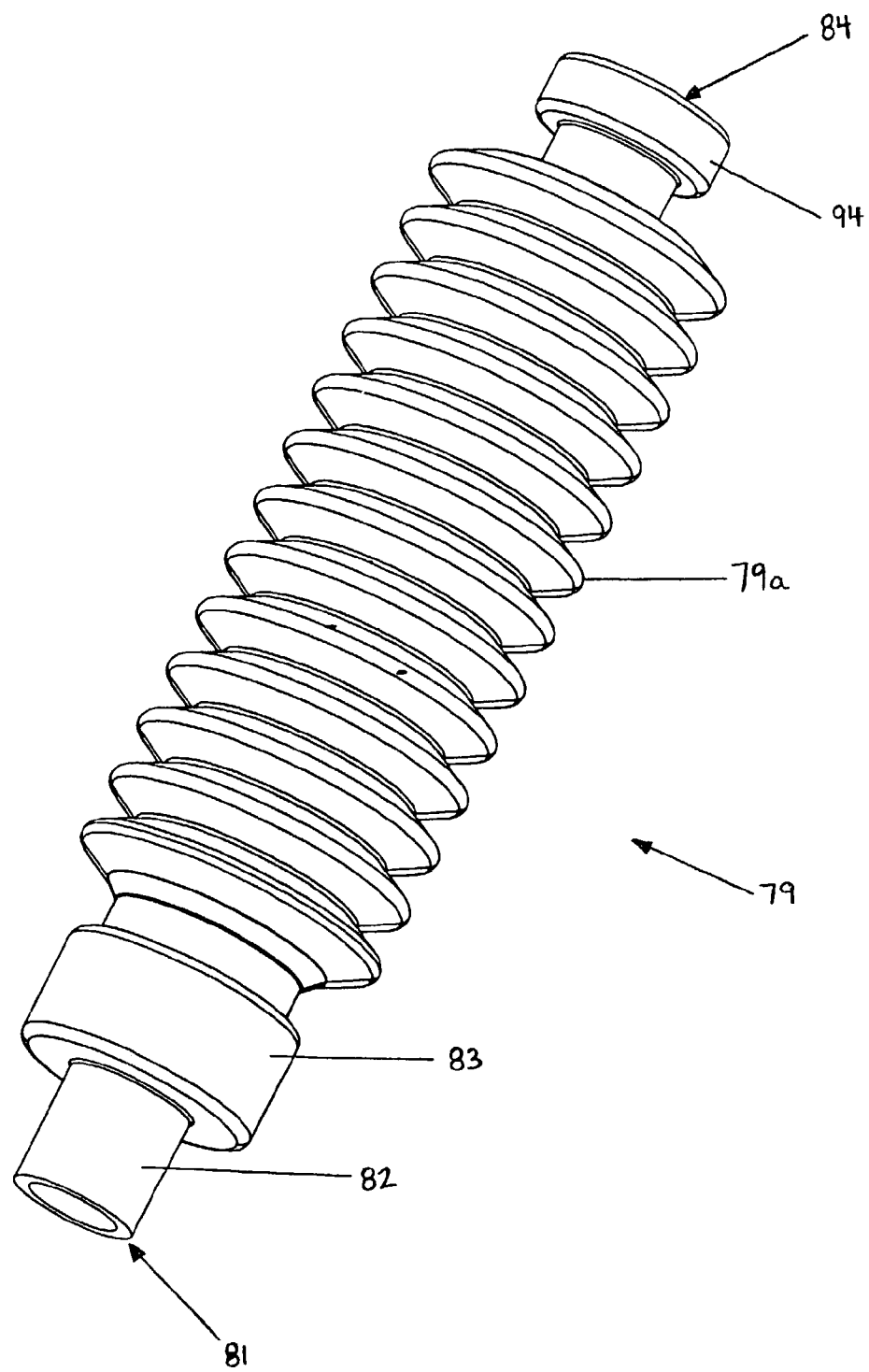
FIG. 10 is a drawing of the container of the multiple-dose syringe of FIG. 9.
Figure 19:
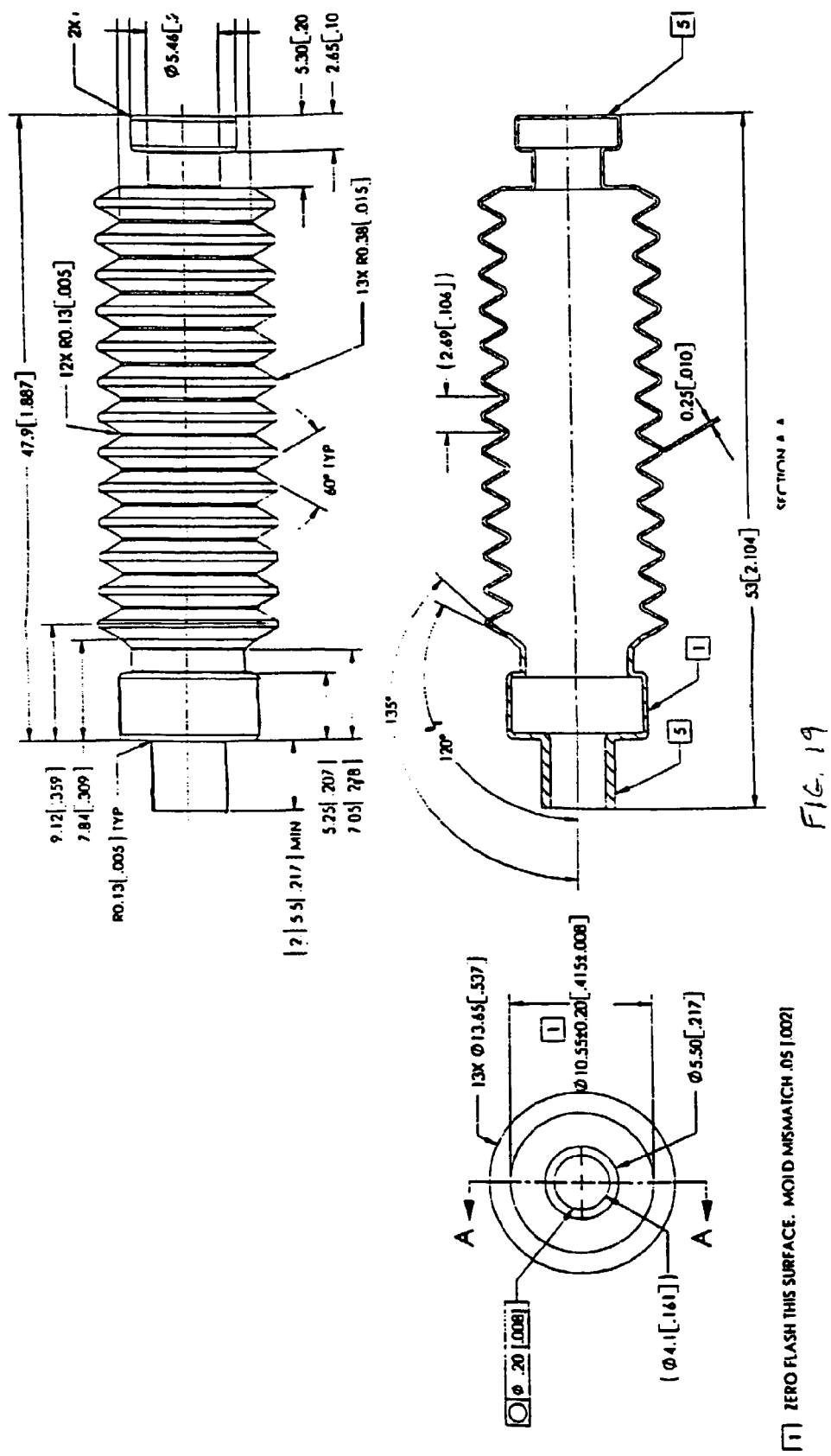
FIG. 19 shows a side, side cut-away, and end view of the container of FIG. 10.

The fluid container 79 is shown in more detail in FIGS. 10 and 19. As shown in FIGS. 9, 9a and 10, the fluid container 79 has a cylindrical bellows-like collapsible shell 79a. The above discussion regarding the construction of shell 30 apply equally to shell 79a, unless noted otherwise below. Fluid container 79 has an open end 81 and a closed end 84. As shown in FIG. 10, at the open end 81, there is a neck portion 82, and a sealing portion 83, which is larger in diameter than neck portion 82. While various manufacturing methods will be apparent to those skilled in the art, the preferred method of manufacturing the fluid container 79 is by blow molding since this method will yield a container with an approximately consistent wall cross-sectional area. Low density polyethylene (LDPE) is most appropriate given the desire for flexibility and the possibility for radiation sterilization. Ethyl Vinyl Acetate (EVA) preferably may be added in a small percentage to enhance flexibility.

Figure 11:
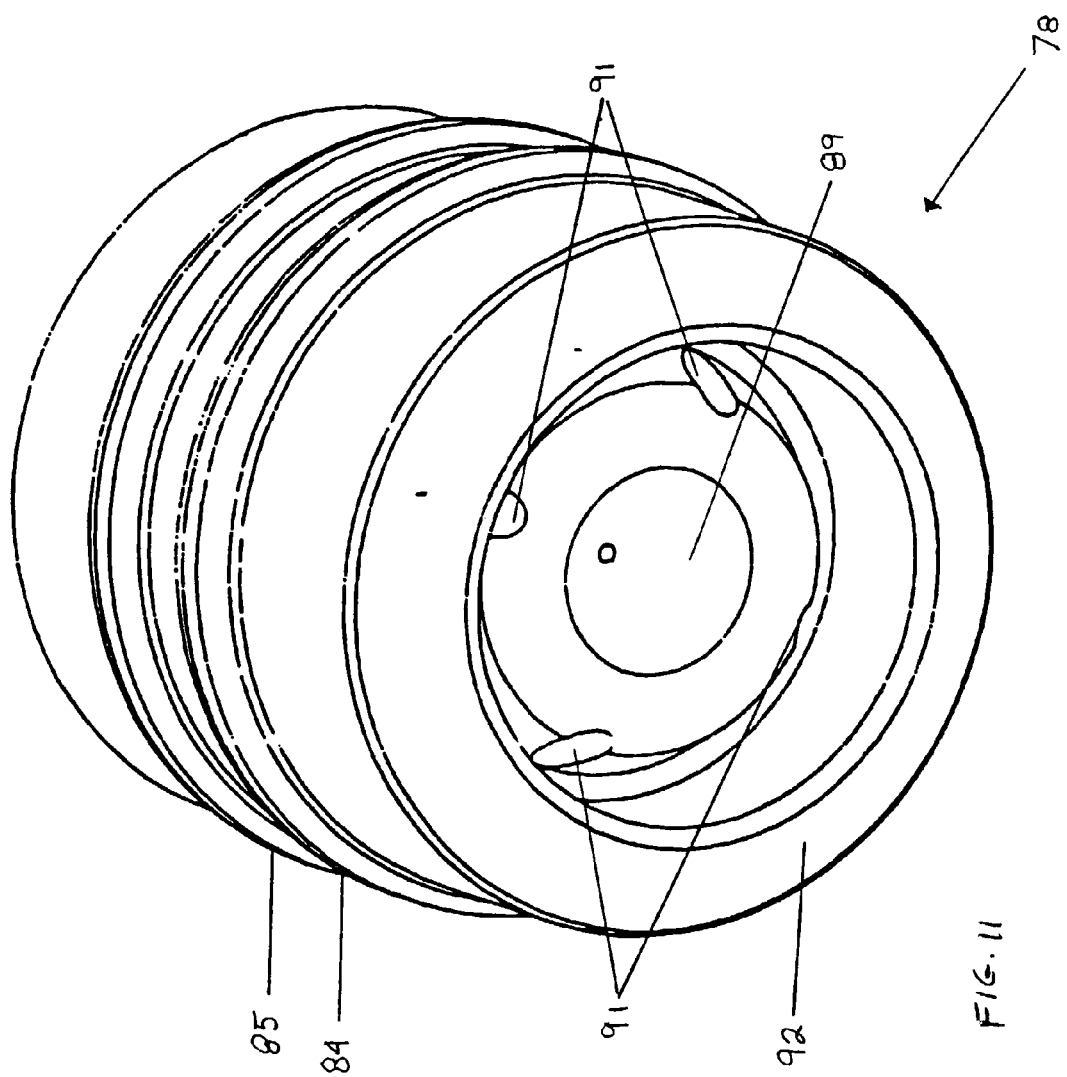
FIG. 11 is a drawing of the closure member of the multiple-dose syringe of FIG. 9.
Figure 12:
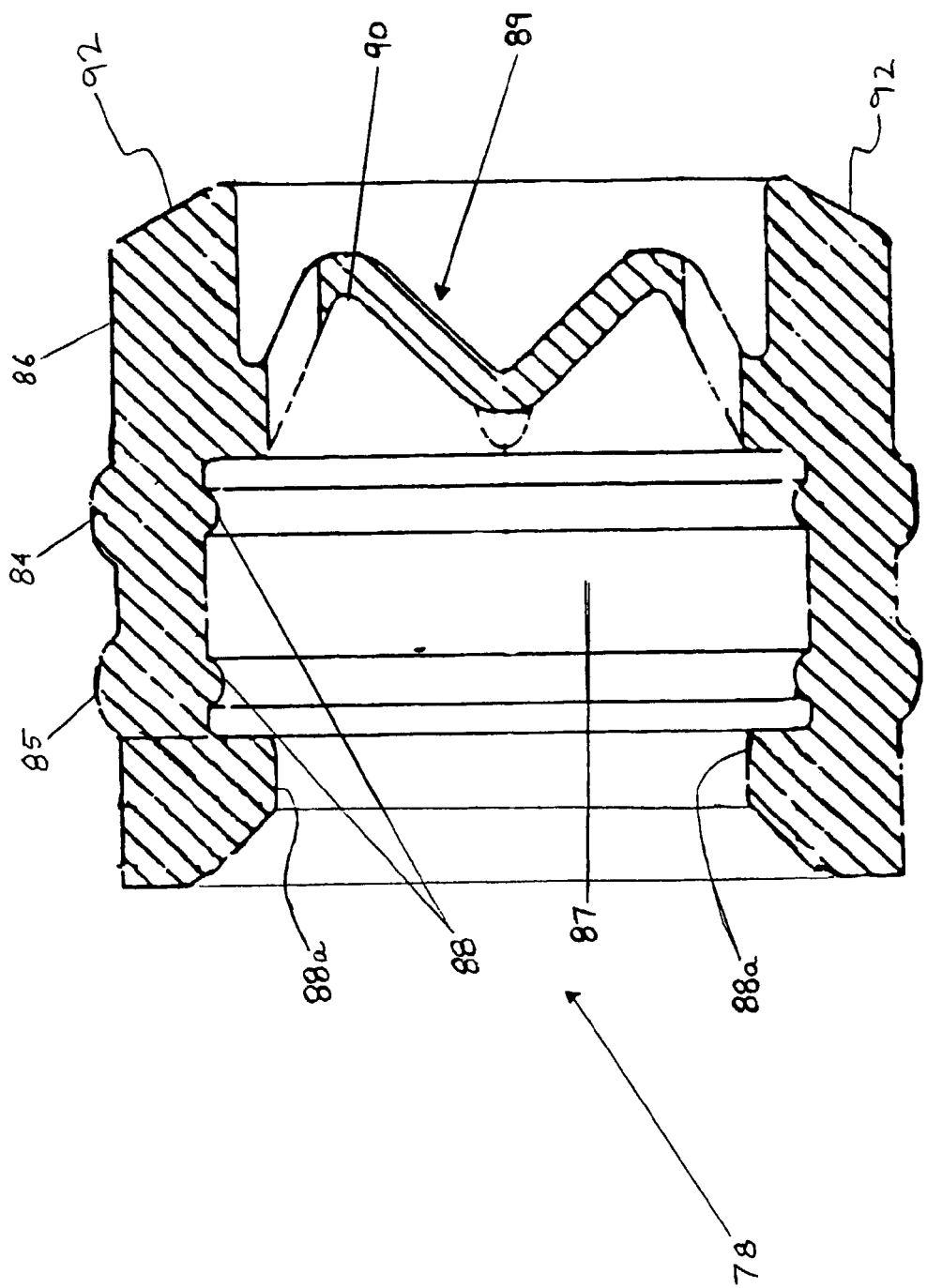
FIG. 12 is a cross sectional view of the closure member of FIG. 11.

The closure member 78 is shown in more detail in FIGS. 11 and 12. The closure member 78 preferably is made either of a synthetic rubber (such as polyisoprene) or silicone. Other materials will be readily apparent to these skilled in the art. Since silicone is more compatible with the preferred method of gamma sterilization, silicone is the preferred material. A silicone material of a low durometer value is preferred to provide the necessary stretch (for the proper operation of the valve portion described below) and a wide compression range (for proper operation of the various sealing ribs described below).

As shown in FIG. 11, the closure member 78 has two external sealing ribs, a primary sealing rib 84 and a secondary sealing rib 85. When the closure member is slideably received into barrel 12 through open end 16 (as shown in FIG. 9), because the sealing ribs are of slightly greater diameter than the inner diameter of the barrel, a sealing force is concentrated to the localized area of the sealing ribs 84 and 85, thereby optimizing sealing pressure and minimizing the frictional load. The sealing rib 84 closest (when assembled as shown in FIG. 9) to the injection port 22 is the primary seal, and is preferably higher relative to the surface 86 of the closure member 78 than the secondary sealing rib 85. Since the primary sealing rib 84 is higher, it undergoes the greatest compression (when assembled into the barrel 12). The secondary sealing rib 85, being slightly lower, provides a redundant seal without doubling the frictional load. The secondary sealing rib 85 also acts as a wiping seal to protect the primary sealing rib 84 from accidental environmental particulate exposure. Preferably, as shown in FIG. 12, both the primary sealing rib 84 and the secondary sealing rib 85 have a flat contact portion bordered by tangent radii to reduce the likelihood of seal extrusion under pressure. It should be understood that the closure member 78 accomplishes the function of sealing between the fluid container 79 and the barrel 12, or, alternatively, this function could be performed by a separate member.

Turning to the interior of the closure member 78, as shown in FIG. 12, the closure member 78 has an interior cavity 87 adapted to receive the neck portion 82 and the sealing portion 83 of the fluid container 79. The closure member 78 has two internal sealing ribs 88 in the interior cavity 87. The closure member 78 also has a shoulder 88a. When the fluid container 79 is assembled as shown in FIGS. 9 and 9a into the closure member 78, the two sealing ribs 88 are compressed and engaged by the sealing portion 83 (shown in FIG. 10), thereby forming a fluid-tight seal. Alternatively, one seal or three or more sealing ribs could be used. In addition, other sealing means will be readily apparent to those skilled in the art, and are included within the invention claimed herein. When assembled as shown in FIG. 9a, the closure member 78 is held on the fluid container 79 by the engagement of the shoulder 88a with the sealing portion 83.

When assembled (as shown in FIGS. 9 and 9a), the fluid container 79 is selectively sealed by the closure member 78. In addition, when assembled, there exists a first cavity (like first region 52, FIG. 1) between the closure member 78 and the injection point 22, and a second cavity inside the fluid container 79. The seal formed by the closure member 78 as to the fluid container 79 is selective because the closure member 78 seals a second fluid in the fluid container 79 but allows the second fluid in the fluid container 79 to be expelled when the fluid pressure differential across the closure member 78 (between the first and second cavities) exceeds a predetermined limit.

To allow expulsion of liquid from the fluid container 79 when the pressure differential across the closure member 78 exceeds a predetermined limit, the closure member 78 includes a valve 89 (shown in FIGS. 11 and 12), which functions as a valve that resembles in operation a poppett or diaphragm valve. The closure member 78 also includes a boss portion 92. The valve 89 is recessed into the closure member 78 as shown in FIGS. 11 and 12, being surrounded by the boss portion 92.

The valve 89 has an interior sealing surface 90 as shown in FIG. 12. The valve 89 of closure member 78 also has several holes, and in the preferred embodiment, four holes 91 as shown in FIG. 11. When assembled as shown in FIGS. 9, 9a, and 9b, the neck portion 82 engages the sealing surface 90 of valve 89 of closure member 78. In addition, the length of the neck portion 82 and the location of the valve 89 are such that, when assembled, the neck portion 82 stretches the valve 89 of the closure member 78, towards the boss portion 92. This stretch creates a resisting force within the valve 89, and the resulting force against the neck portion 82 creates a pre-load pressure that serves to contain the second fluid in the fluid container 79 until a predetermined pressure differential across the valve 89 is exceeded. As shown in FIGS. 9a and 9b, the valve 89 when assembled is of a flatter shape than that shown in FIG. 12 due to the stretching of the valve 89.

As shown in FIGS. 9 and 10, the fluid container 79 has a protuberance 94 at the closed end of 84 for engaging a slot 93 in the plunger 80 defining a cavity to contain a fluid. When assembled as shown in FIGS. 9, 9a, and 9b, the fluid container 79 is connected to the plunger 80. Also shown in FIG. 9, the thumb pad 81 is separate from the elongate shaft 81a, and engages by a snap-fit to the elongate shaft 81a. However, as readily apparent to one skilled in the art, the plunger 80 could be an integral component having a thumb pad and elongate shaft as shown in FIGS. 1–3. Alternatively, instead of a protuberance 94 and slot 93, a coupler 34 as previously described (in FIG. 5) could be used. It is also contemplated that the plunger 80 and the fluid container 79 could be formed as an integral component.

In operation, when assembled as shown in FIGS. 9, 9a, and 9b, the multiple-dose syringe 77 functions similarly to the multiple-dose syringe 10 described above. An operator loads the desired amount of a first or primary fluid (such as a medicine) for injection into the syringe 77 similar to loading a conventional syringe, that is, by retracting the plunger 80. The fluid container 79 will preferably be pre-filled with a secondary fluid, for example, saline. Alternatively, the fluid container could be loaded by a user with the secondary fluid prior to assembling the syringe 77. After fluidly connecting the syringe to an IV (using either a needle-less system such as those discussed above or a needle), the fluid held in the barrel 12 is expelled from the barrel by pressing on the thumb pad 81 until the boss portion 92 contacts the closed end 14 of the barrel 12, thereby having expelled virtually all of the first fluid. The valve 89 of the closure member 78 is recessed so as to protect the valve 89 from impact with the closed end 14 of the barrel 12. Upon impact of the boss portion 92 of the closure member 78, the user will continue to apply pressure to the thumb pad 81, thereby causing a pressure differential across the valve 89, which pressure differential is greater than that present during expulsion of the first fluid from the barrel 12. The greater pressure differential causes the valve 89 to stretch a small additional amount, thereby allowing the second fluid held in the fluid container 79 to flow from the fluid container 79 through the holes 91 of the closure member 78, and into and through the injection port 22, thereby flushing the first fluid.

Figures 13A, 13B:
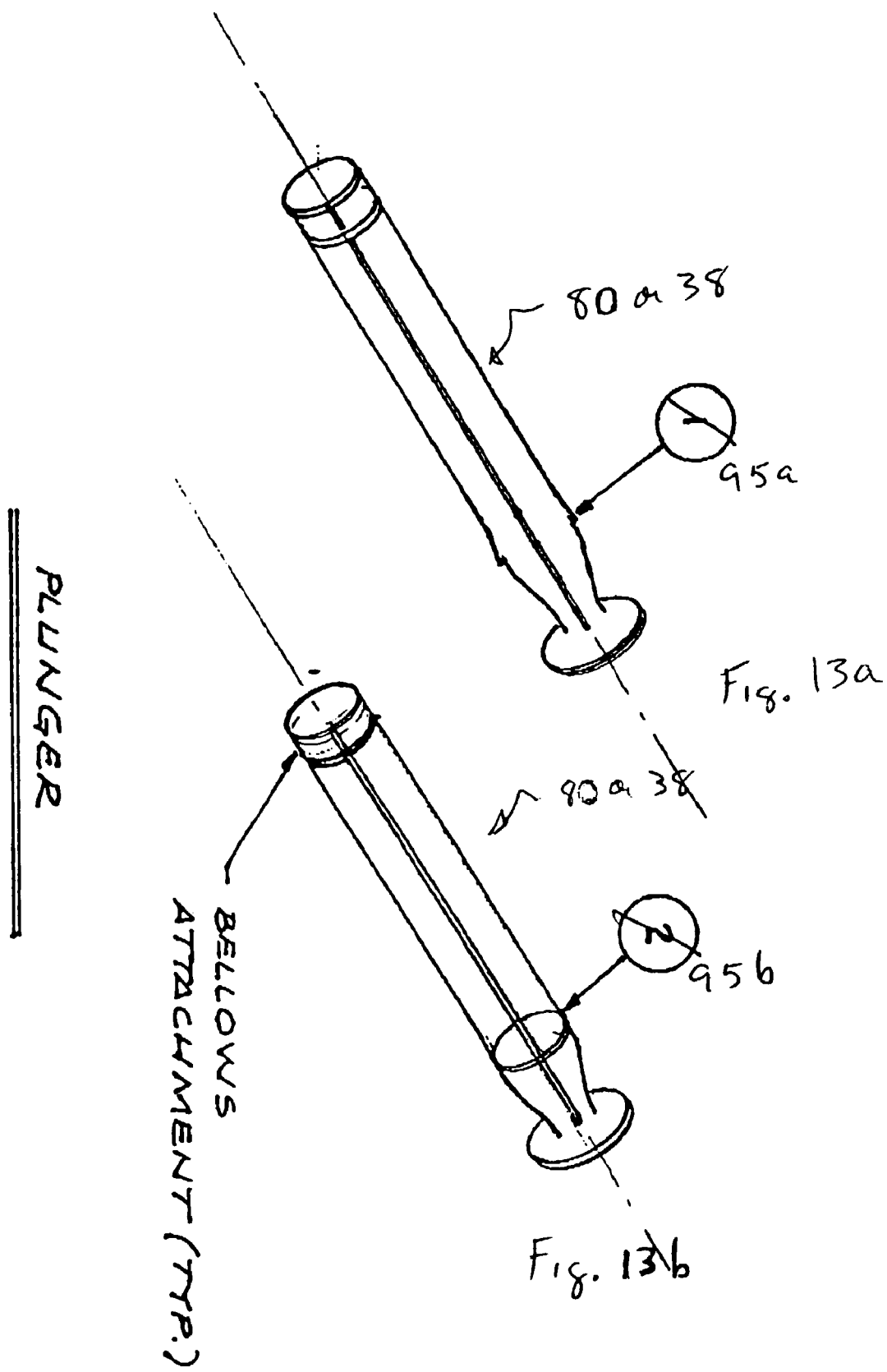
FIG. 13a is a drawing of an alternative embodiment of the plunger of the multiple-dose syringe of FIG. 9 having a detent in the form of a triangle.
FIG. 13b is a drawing of an alternative embodiment of the plunger of the multiple-dose syringe of FIG. 9 having a detent in the form of a circular disk.
Figure 13C:
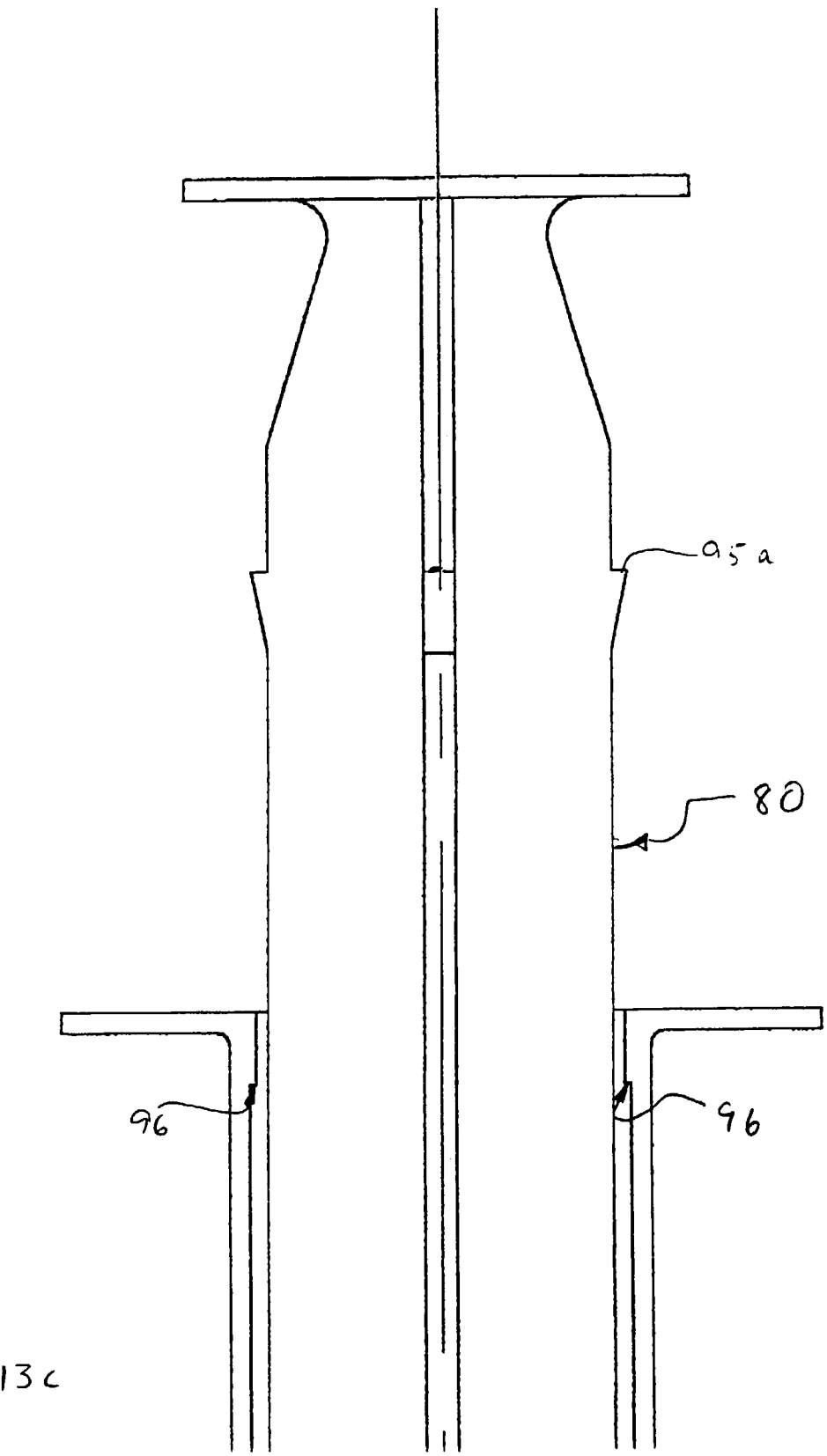
FIG. 13c is a drawing illustrating an assembly of the plunger shown in FIG. 13a with a conventional barrel.

In the operation of the multiple dose syringe 77 described above, as well as in the operation of the multiple-dose syringe 10 described above, once all of the fluid has been expelled from the fluid container 79, (or, alternatively, 28) it has been found that the bellows-type fluid container 79 (or 28) may tend to move a small amount toward its original position due to the spring-like nature of the bellows. This tendency is undesirable because it tends to aspirate a small amount of fluid into the syringe. To counteract and prevent this movement, in one alternative embodiment of plunger 80 (or 38), a detent 95 in the form of a triangle (95a shown in FIGS. 13a and 13c) or a circular disk (95b, shown in FIGS. 9a and 13b) has been added as shown in FIGS. 13a, 13b, and 13c respectively. Other variations will be readily apparent. A conventional barrel 12 has a ridge or ring 96 (shown in FIGS. 9a and 13c). The apparent purpose of the ridge or ring 96 of the conventional barrel 12 is to prevent or at least discourage a user from pulling the plunger 80 (or 38) completely out of the barrel 12 by acting as a stop for a conventional plunger. The detent 95 is located such that the detent will snap past the circular ridge or ring 96 that is present on a conventional barrel 12 when the plunger 80 (or 38) is fully depressed. The detent 95 is sized such that the user may readily push the detent 95 past the ridge or ring 96 of the barrel 12, but the spring action of the bellows-type fluid container (79 or 28) is insufficient to push the detent 95 across the ridge or ring 96 toward the open end of the barrel 12.

As an alternative embodiment to the closure member in the form of a cap 44 shown in FIG. 6, as an alternative to the cap structure 62 shown in FIG. 7, and as an alternative to the closure member 78 shown in FIGS. 9, 11, and 12, FIG. 14 shows the fluid container 28 closed by a closure member including a valve 141. The valve 141 is preferably a valve that opens when the pressure in the container 28 exceeds some desired level (with respect to the pressure in the first region 52). One embodiment of the valve 141 operates much like a "Heimlich"-type valve, which is well known in the medical arts. The "Heimlich" valve was described in U.S. Pat. No. 3,463,159. A "Heimlich" valve consists of a pair of elastic membranes or sheets having a slit between them through which fluids may flow in one direction. This type of valve has been used in a variety of industries, see, e.g., U.S. Pat. No. 4,261,362, and will be readily familiar to a person skilled in the art. A similar valve is found in the well-known "whoopie" cushion found in any toy store. A similar valve has also been referred to as a "condom"-type valve (See U.S. Pat. No. 4,738,672), and could also be used in modified form. The valve 141 may be considered a Heimlich-type valve except that the opposing walls (elements 150 and 151, shown in FIG. 15) of the slit 140 are not as long, i.e., the thickness of valve 141 is not as thick, as the "rubbery tube" of the Heimlich valve shown in the '159 Patent.

In the embodiment shown in FIG. 14, valve 141 consists of a circular elastic membrane with an outer perimeter shaped to form a perimeter seal 50 such as shown in FIG. 6. The valve 141 in FIG. 14 is shown in the closed state. The valve 141 is composed of an elastomer or similar compound, and preferably a butyl or nitryl rubber compound. Other suitable materials will be readily apparent to those skilled in the art. Valve 141 of FIG. 14 includes a slit 140 through the entire thickness (shown for example, as "t" in FIG. 17) of the valve 141. The slit 140 is held closed by the elasticity of the compound. As noted above, pressure in the container 28 is matched by backpressure of the fluid in the first region 52. Therefore, the valve 141 will not open until the fluid in the first region 52 is substantially expelled, as illustrated in FIG. 15. As shown in FIG. 15, the valve 141 is in the open state, as slit 140 is open, allowing fluid to pass from the container 28 into the first region 52.

Figure 16:
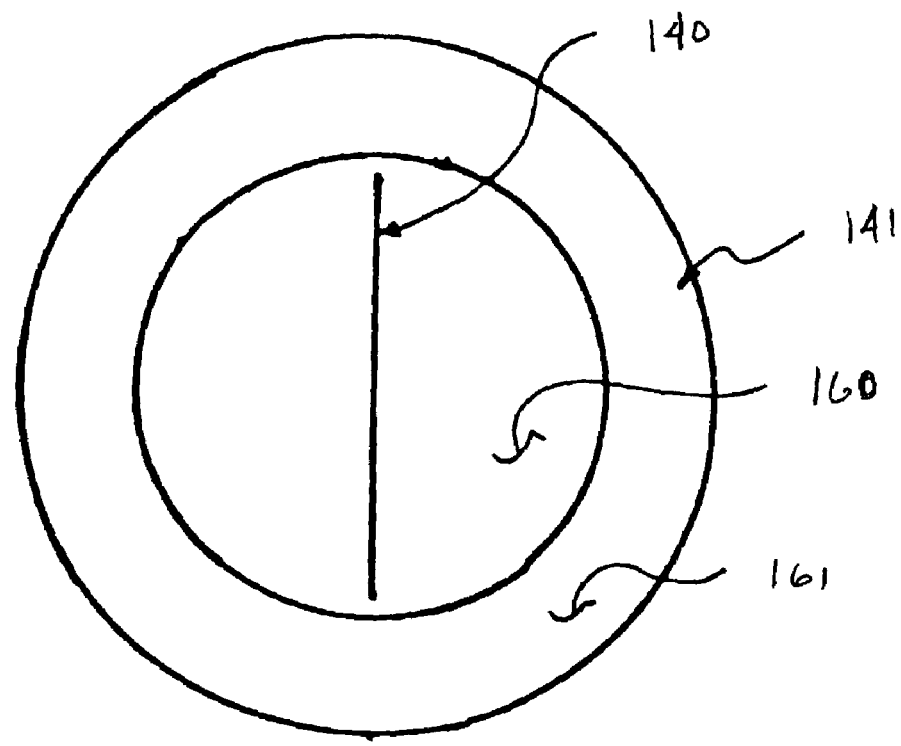
FIG. 16 is a more detailed view of an embodiment of the valve of the syringe of FIG. 9.
Figure 17:
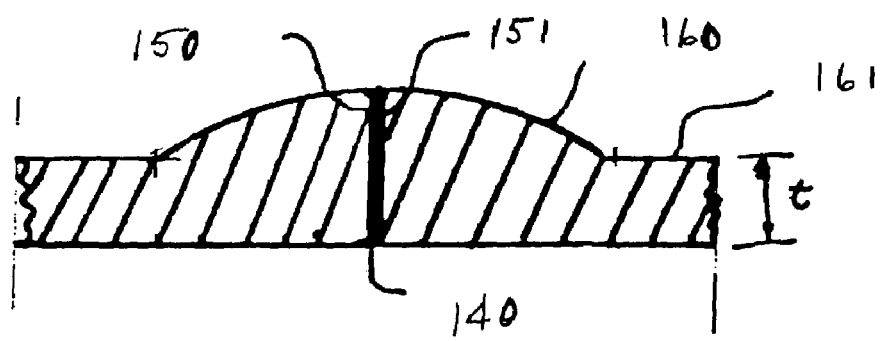
FIG. 17 is a side view of the valve of FIG. 16.

An embodiment of the valve 141 is shown in FIG. 16. It will be apparent to one skilled in the art that the length of the slit 140 and thickness (t, shown in FIG. 17) will depend on the diameter of the container 28. For some sizes, it may be desirable to form a raised region 160 on the outward facing surface 161 (shown in FIG. 16 and FIG. 17). The raised region 160 has a greater thickness than t (shown in FIG. 17). The purpose of the raised region is to provide more surface area for the opposing walls 150 and 151 of the slit 140, thereby providing a better, more positive seal. Other such variations should be apparent to a person skilled in the art.

It should also be understood that the valve 141 may also include a perimeter seal, similar to perimeter seal 50 shown in FIG. 6, and a corresponding flange, similar to flange 48 of FIG. 6, to attach the valve to the container 28. As an alternative, the valve 141 could also be attached to the container 28 as shown in FIG. 7. Alternatively, any other suitable means to attach the valve 141 to the container 28 could be used so long as such means provides a seal between the container 28 and the valve 141 such that fluid substantially only passes through the valve 141, and in the illustrated embodiment, through slit 140. In the embodiments shown in FIGS. 6 and 7, the perimeter seal 50, or alternatively, seal 72, form a seal between the container 28 and the walls of the barrel 12. It should be understood that the valve 141 could be formed to accomplish this function of sealing between the container 28 and the barrel 12, or alternatively, this function could be performed by a separate member. It is contemplated that the plunger 80 or 38 and the container 28 could be formed as a single integral component.

Figure 18:
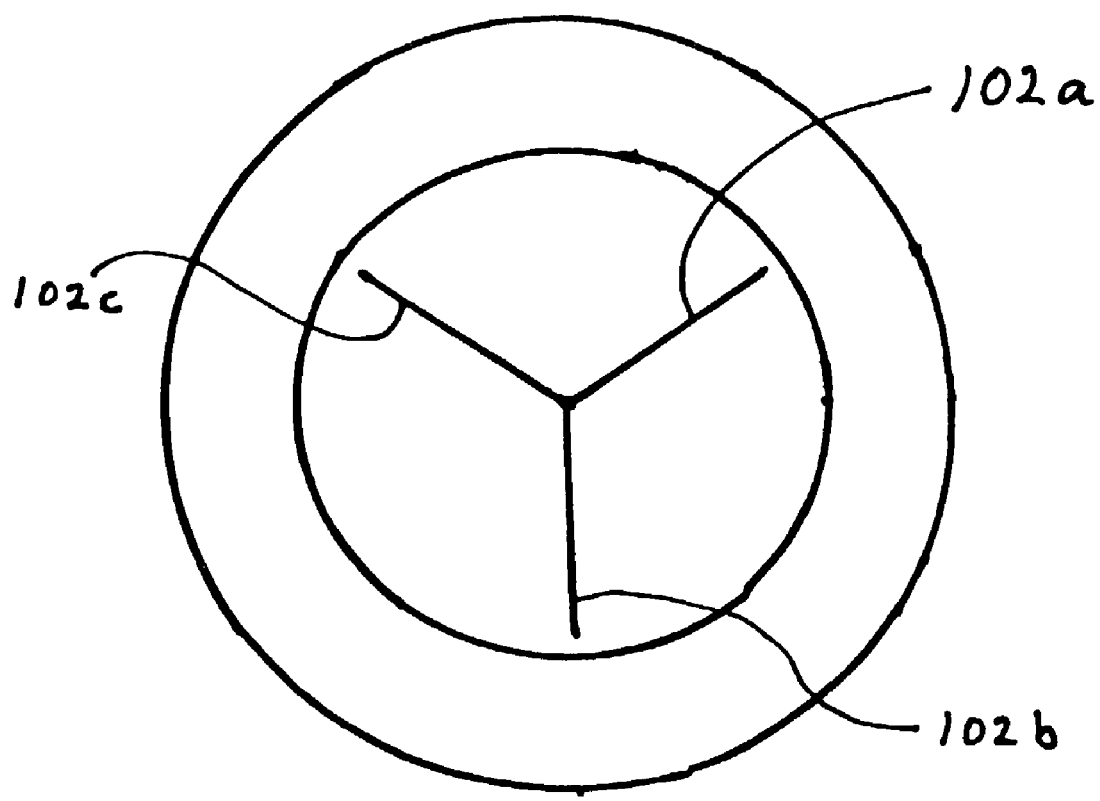
FIG. 18 is an alternative embodiment of the valve of the syringe of FIG. 14.

FIG. 18 illustrates yet another alternative to valve 141 shown in FIGS. 14–17. FIG. 18 illustrates a valve similar to valve 141 discussed above, except that, instead of a single slit 140, the valve of FIG. 18 has three slits 102a–c of equal length, arranged symmetrically as shown. Alternatively, any number of slits could by used, of the same or different length, arranged symmetrically or asymmetrically.

The present invention is not limited to a single slit-type, Heimlich-type, whoopie cushion-type, condom-type, poppett, or diaphrahm valve, but includes any suitable valve that, when included within a closure member attached to the container 28, operates to allow the fluid to pass from the container when the pressure differential across the closure member, or more precisely, the valve, exceeds some desired level.

It can be seen that the inventions described herein provide an economical and easy to use solution to the problem of sequentially injecting two fluids. The simple operation saves time and materials (i.e, one versus two syringes).

As described above, the syringe of the present invention is preferably pre-loaded or filled with saline or other second fluid at the time of manufacture. The plunger is also attached to the container and the resulting assembly is packaged in a sterile condition for shipment. A needle may or may not be attached, depending on the configuration desired. It should be noted that the barrel of the present invention is preferably an unmodified component from a standard syringe design. This eliminates the need to create new and specialized parts for use with a two-fluid syringe. Although it is preferred that the container be pre-loaded in the syringe, it should also be understood that the container could be provided as a separate unit for installation and use with an otherwise standard syringe. This variation is facilitated by use of a design that incorporates one or more unmodified parts from a standard syringe.

The foregoing description of the present invention has been presented for purposes of illustration and description. The specific embodiments thereof as disclosed and illustrated herein are not to be considered in a limiting sense as numerous variations are possible. Applicant regards the subject matter of the invention to include all novel and non-obvious combinations and subcombinations of the various elements, features, functions and/or properties disclosed herein. No single feature, function, element or property of the disclosed embodiments is essential. Consequently, the invention and modifications commensurate with the above teachings and skill and knowledge of the relevant art are within the scope of the present invention. It is intended that the description be construed to include all alternative embodiments as permitted by the prior art.

What is claimed is:

1. A multiple-dose syringe comprising:
    a barrel having a closed end and an open end, the closed end having an injection port;
    a plunger having a first end and a second end; and
    a container having a collapsible shell, the collapsible shell having a first end and a second end and defining a first cavity for holding a first dose of a fluid, the first end having an opening, the opening being selectively sealed by a closure member including a valve, the valve opening in response to a fluid pressure differential across the valve, the container slideably positioned within the barrel with the first end having the opening in closer proximity to the injection port of the barrel than the second end, the second end of the container being connected to the first end of the plunger, the container being movable by the plunger from a first drawn position with the first end of the collapsible shell being a distance away from the injection port to a compressed position with the opening in the first end adjacent to the injection port of the barrel, the first end of the collapsible shell of the container and the barrel defining a second cavity for holding a second dose of a fluid, which second dose is expelled through the injection port when the container is moved from the drawn position toward the compressed position by the plunger.

2. A container for use with a syringe having a barrel and a plunger, the barrel having an interior surface, an injection port, and an open-end, the plunger having a first and second end, the first end being adapted to engage the container, the container comprising:
    a collapsible shell defining a first interior cavity for holding a first dose of a fluid, and having an outer surface and an open end, the collapsible shell configured to fit within the barrel of the syringe, and further configured to engage the first end of the plunger of the syringe; and
    a valve to selectively seal the open end of the container, the valve opening in the presence of a fluid pressure differential across the valve;
    whereby the interior surface of the barrel and the outer surface of the collapsible shell when engaged with the first end of the plunger and placed in the barrel defines a second cavity for holding a second dose of a fluid to be expelled through the injection port of the barrel.

3. A multiple-dose syringe comprising:
    a barrel having a closed end and an open end, the closed end having an injection port;
    means for selectively containing a first dose of a fluid, the containing means having at least one opening, the containing means being collapsible when compressed in the barrel;
    means for selectively sealing the at least one opening of the containing means, the sealing means opening in response to a fluid pressure differential; and
    means for compressing the containing means within the barrel;
    wherein the containing means is slideably positioned within the barrel to move from a drawn position to a compressed position with the at least one opening in proximity to the injection port of the barrel, the compressing means engages the containing means in the barrel, the containing means and barrel define a cavity for holding a second dose of a fluid, and the second dose is expelled through the injection port when the containing means is moved toward the compressed position.

* * * * *